(12) United States Patent
Su et al.

(10) Patent No.: US 8,124,187 B2
(45) Date of Patent: Feb. 28, 2012

(54) METHODS OF FORMING POROUS COATINGS ON SUBSTRATES

(75) Inventors: Cheyenne Xiaoyan Su, Forest Grove, OR (US); David L. Walker, Camas, OR (US)

(73) Assignee: Viper Technologies, Portland, OR (US)

( * ) Notice: Subject to any disclaimer, the term of this patent is extended or adjusted under 35 U.S.C. 154(b) by 332 days.

(21) Appl. No.: 12/555,440

(22) Filed: Sep. 8, 2009

(65) Prior Publication Data

US 2011/0059268 A1    Mar. 10, 2011

(51) Int. Cl.
  *B05D 3/02* (2006.01)
(52) U.S. Cl. .................................. 427/376.1
(58) Field of Classification Search ............. 427/376.1
  See application file for complete search history.

(56) References Cited

U.S. PATENT DOCUMENTS

| | | | |
|---|---|---|---|
| 2,478,420 A | 8/1949 | Payson | |
| 2,593,943 A * | 4/1952 | Wainer | 419/37 |
| 3,155,502 A | 1/1967 | Broodo | |
| 3,330,892 A | 7/1967 | Herrmann | |
| 3,725,142 A | 4/1973 | Huseby | |
| 3,802,939 A | 4/1974 | Ohtani et al. | |
| 3,841,848 A | 10/1974 | Kasai et al. | |
| 3,864,809 A | 2/1975 | Donachie | |
| 4,284,121 A | 8/1981 | Horton | |
| 4,457,851 A | 7/1984 | Tabaru et al. | |
| 4,478,790 A | 10/1984 | Huther et al. | |
| 4,606,767 A | 8/1986 | Nagato | |
| 4,644,942 A | 2/1987 | Sump | |
| 4,721,599 A | 1/1988 | Nakamura | |
| 4,765,950 A | 8/1988 | Johnson | |
| 4,854,496 A | 8/1989 | Bugle | |
| 4,964,907 A | 10/1990 | Kiyota et al. | |
| 5,022,935 A | 6/1991 | Fisher | |
| 5,034,186 A | 7/1991 | Shimamune et al. | |
| 5,104,410 A | 4/1992 | Chowdhary | |
| 5,159,007 A | 10/1992 | Saitoh et al. | |
| 5,194,203 A | 3/1993 | Kankawa et al. | |
| 5,211,775 A | 5/1993 | Fisher et al. | |
| 5,308,576 A | 5/1994 | Green et al. | |

(Continued)

FOREIGN PATENT DOCUMENTS

JP        60-216512        10/1985

(Continued)

OTHER PUBLICATIONS

Johnson, John L., "Mass Production of Medical Devices by Metal Injection Molding", Medical Device & Diagnostics Industry, Nov. 2002, 5 pages.

(Continued)

*Primary Examiner* — Nathan Empie
(74) *Attorney, Agent, or Firm* — Mohr Intellectual Property Law Solutions, PC

(57) ABSTRACT

Methods of forming porous coatings on substrates. Methods of forming porous coatings include preparing a binder, applying the binder to a substrate to form a binder layer, applying a coating material to the binder layer to form a coating material layer, and sintering the coated substrate. In some examples, preparing a binder includes mixing together metal particles including titanium hydride or cobalt disilicide, a polymer including polybutene or poly-isobutylene, a brazing agent, and methyl cellulose. In some examples, the coating material includes titanium or cobalt. Applying the binder may include spray coating the binder onto the substrate.

26 Claims, 7 Drawing Sheets

U.S. PATENT DOCUMENTS

| | | | |
|---|---|---|---|
| 5,338,508 A | | 8/1994 | Nitta et al. |
| 5,403,374 A | | 4/1995 | Kitagawa et al. |
| 5,403,411 A | | 4/1995 | Smith et al. |
| 5,441,695 A | | 8/1995 | Gladden |
| 5,443,510 A | | 8/1995 | Shetty et al. |
| 5,464,670 A | | 11/1995 | Ikuma et al. |
| 5,545,248 A | | 8/1996 | Tokumoto et al. |
| 5,665,289 A | | 9/1997 | Chung et al. |
| 5,733,580 A | | 3/1998 | Ikuma et al. |
| 5,738,817 A | | 4/1998 | Danforth et al. |
| 5,782,954 A | | 7/1998 | Luk |
| 5,848,350 A | | 12/1998 | Bulger |
| 5,854,379 A | | 12/1998 | Takayama et al. |
| 6,027,686 A | | 2/2000 | Takahashi et al. |
| 6,075,083 A | | 6/2000 | Peiris |
| 6,132,674 A | * | 10/2000 | Compton et al. ............... 419/2 |
| 6,261,322 B1 | | 7/2001 | Despres, III et al. |
| 6,306,196 B1 | | 10/2001 | Date et al. |
| 6,376,585 B1 | | 4/2002 | Schofalvi et al. |
| 6,534,197 B2 | | 3/2003 | Noda et al. |
| 6,544,472 B1 | | 4/2003 | Compton et al. |
| 6,555,051 B1 | | 4/2003 | Sakata et al. |
| 6,649,682 B1 | * | 11/2003 | Breton et al. ............... 524/404 |
| 6,689,311 B2 | | 2/2004 | Morita et al. |
| 6,725,901 B1 | | 4/2004 | Kramer et al. |
| 6,759,004 B1 | | 7/2004 | Dwivedi |
| 6,770,114 B2 | | 8/2004 | Bartone et al. |
| 6,846,862 B2 | | 1/2005 | Schofalvi et al. |
| 6,849,229 B2 | | 2/2005 | Ott et al. |
| 6,939,488 B2 | | 9/2005 | Blomacher et al. |
| 6,945,448 B2 | | 9/2005 | Medlin et al. |
| 7,063,815 B2 | | 6/2006 | Li et al. |
| 7,285,241 B2 | | 10/2007 | Puide |
| 7,328,831 B1 | * | 2/2008 | Topolski ............... 228/227 |
| 2004/0133283 A1 | | 7/2004 | Shetty |
| 2005/0048193 A1 | | 3/2005 | Li et al. |
| 2005/0196312 A1 | | 9/2005 | Nyberg et al. |
| 2005/0276687 A1 | * | 12/2005 | Ford et al. ............... 415/173.1 |
| 2006/0004466 A1 | | 1/2006 | Glocker et al. |
| 2006/0018780 A1 | | 1/2006 | Hosamani et al. |
| 2006/0052880 A1 | | 3/2006 | Brosnahan, III et al. |
| 2006/0285991 A1 | | 12/2006 | McKinley |
| 2007/0065329 A1 | | 3/2007 | Nyberg et al. |
| 2007/0068340 A1 | | 3/2007 | Nyberg et al. |
| 2007/0154620 A1 | | 7/2007 | Lawrynowicz et al. |
| 2007/0196230 A1 | | 8/2007 | Hamman et al. |

FOREIGN PATENT DOCUMENTS

| | | |
|---|---|---|
| JP | 04-116104 | 4/1992 |
| JP | 06002011 | 1/1994 |
| JP | 07-090318 | 4/1995 |
| JP | 09-013153 | 1/1997 |
| JP | 09-148166 | 6/1997 |

OTHER PUBLICATIONS

Nyberg, Eric, "New Titanium MIM Process", Expanded Stories From PM Newsbytes, Sep. 11, 2006, 1 page.

Weil et al., K. Scott, "A New Binder for Powder Injection Molding Titanium and Other Reactive Metals", Journal of Materials Processing Technology, vol. 176, Issues 1-3, Jun. 6, 2006, p. 205-209.

Weil et al., K. Scott, "Manufacturers 'Need Better Quality Titanium PM Powders'", Metal Powder Report, vol. 60, Issue 10, Oct. 2005, p. 8-13.

United States Patent and Trademark Office, "First Office Action", Sep. 17, 2010.

* cited by examiner

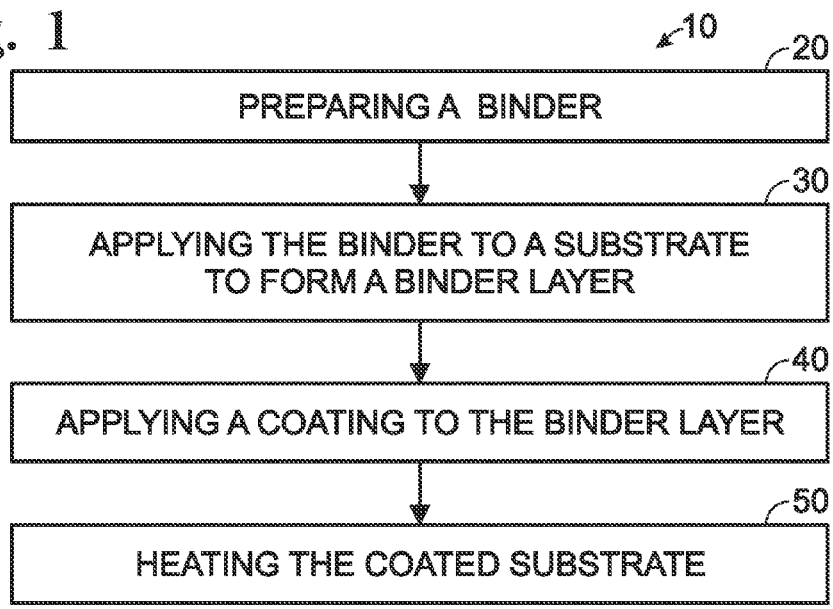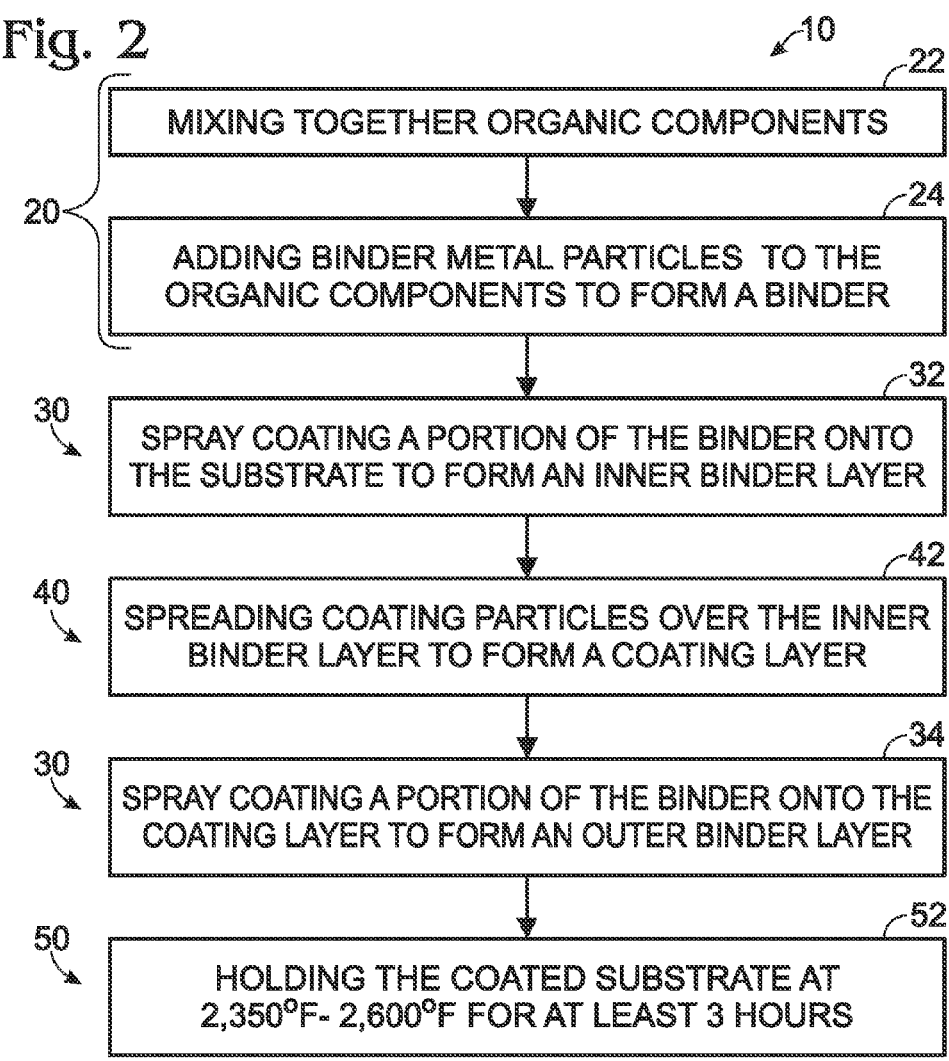

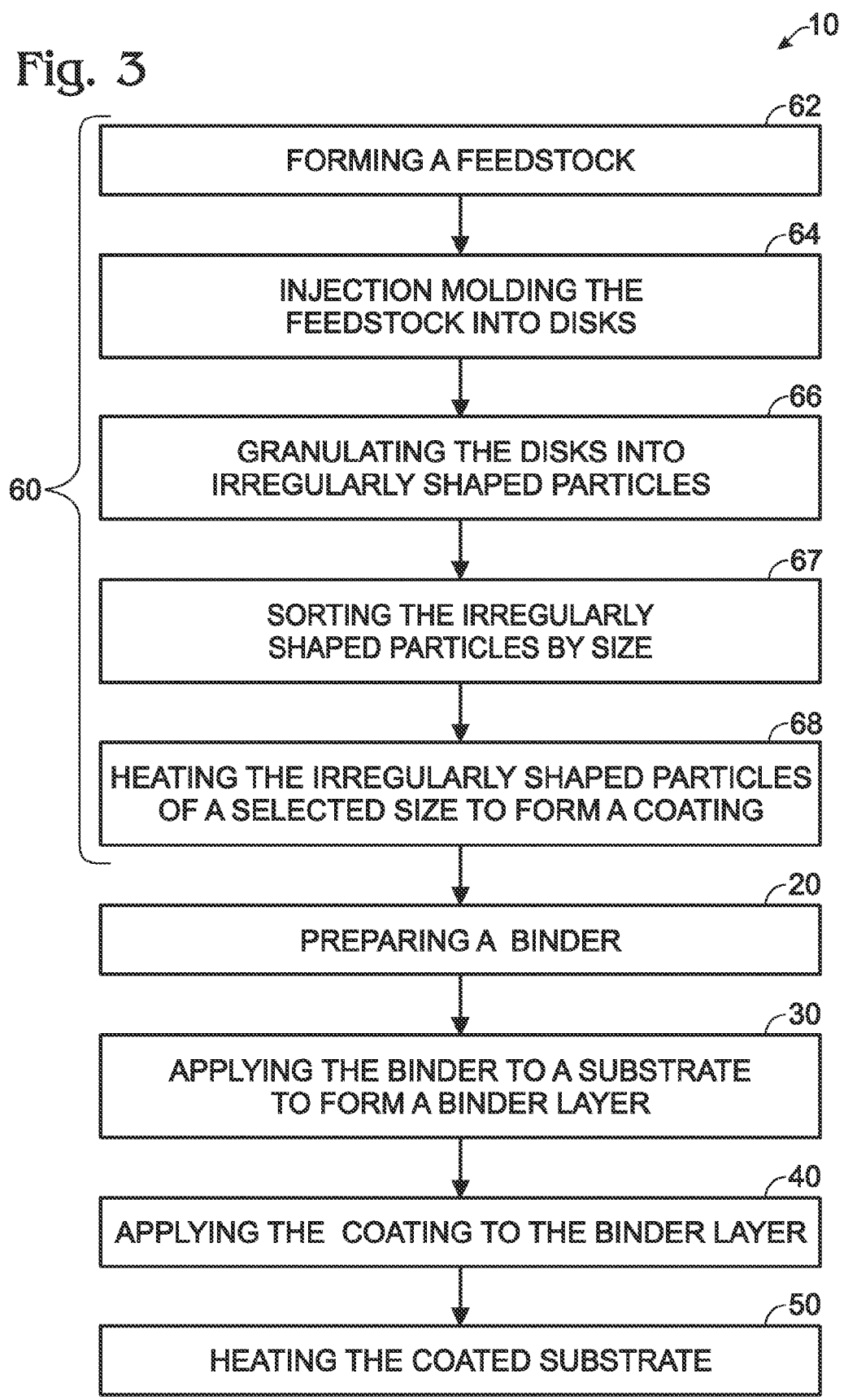

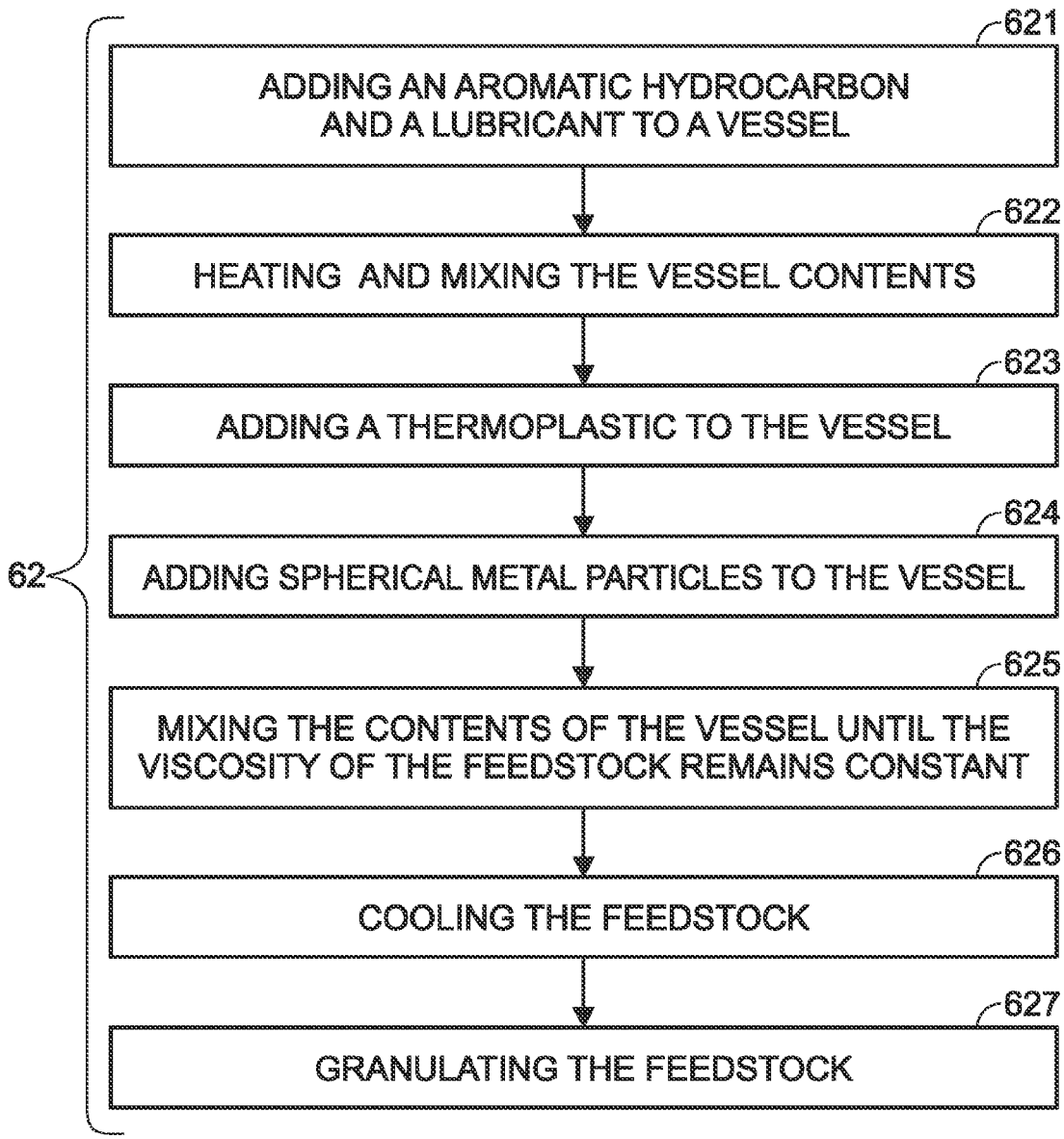

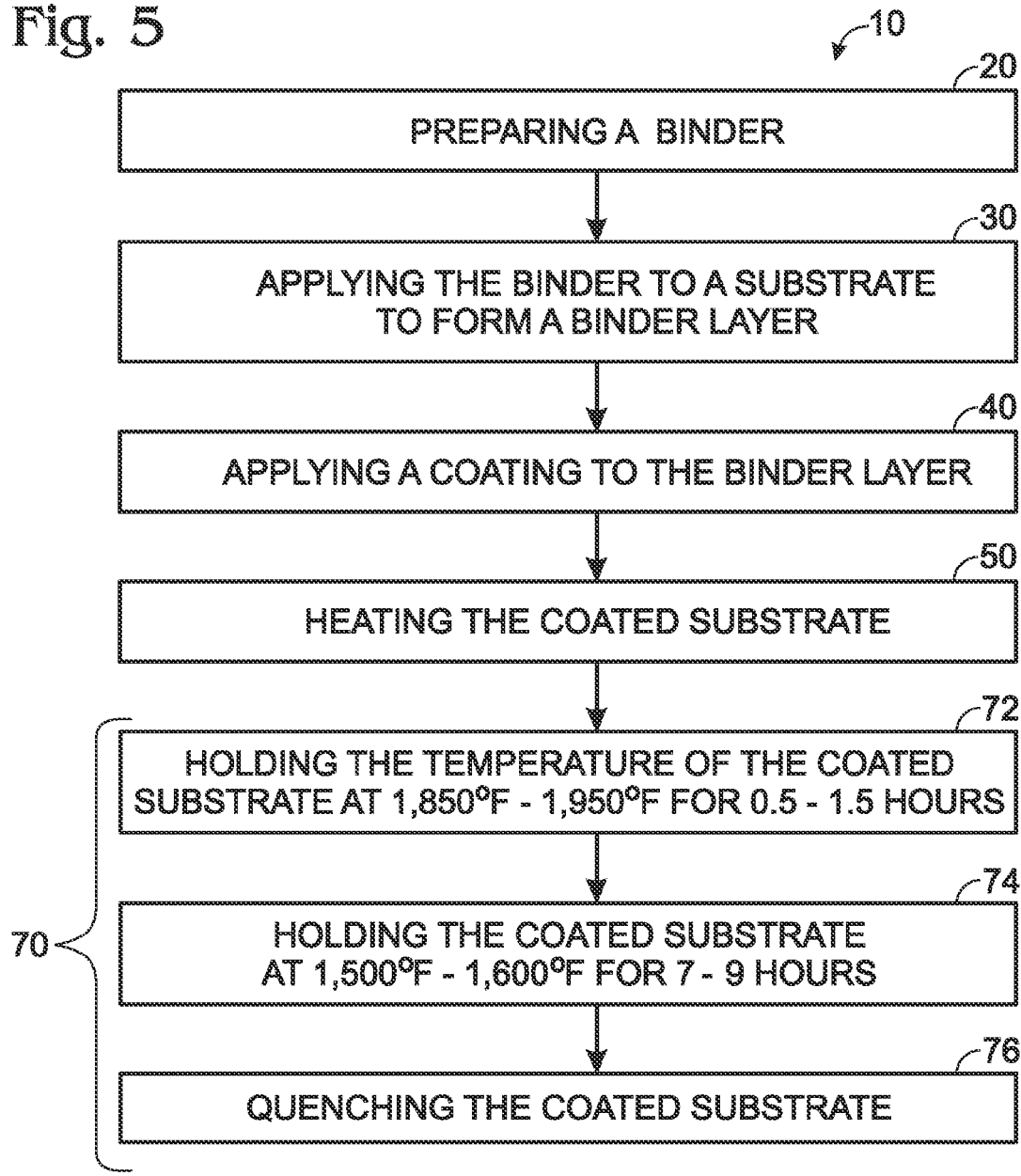

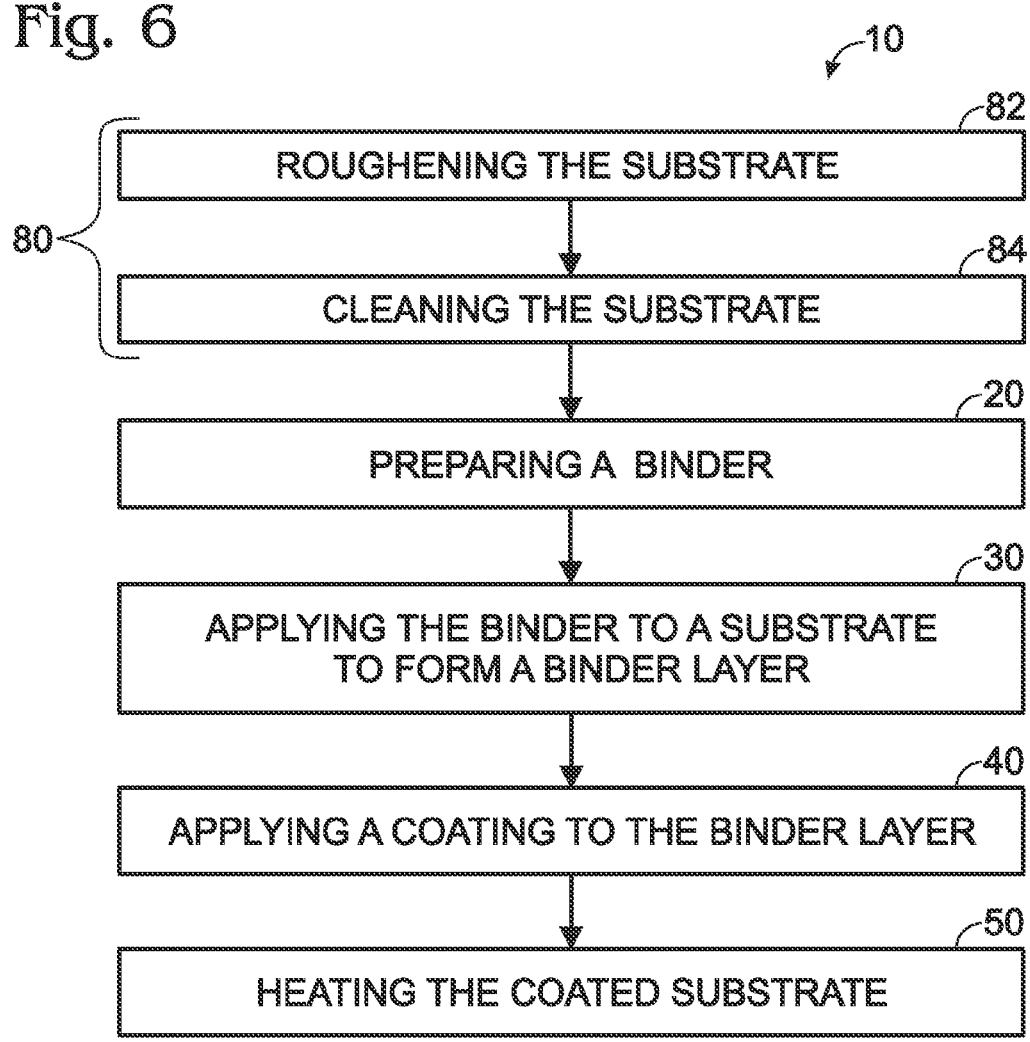

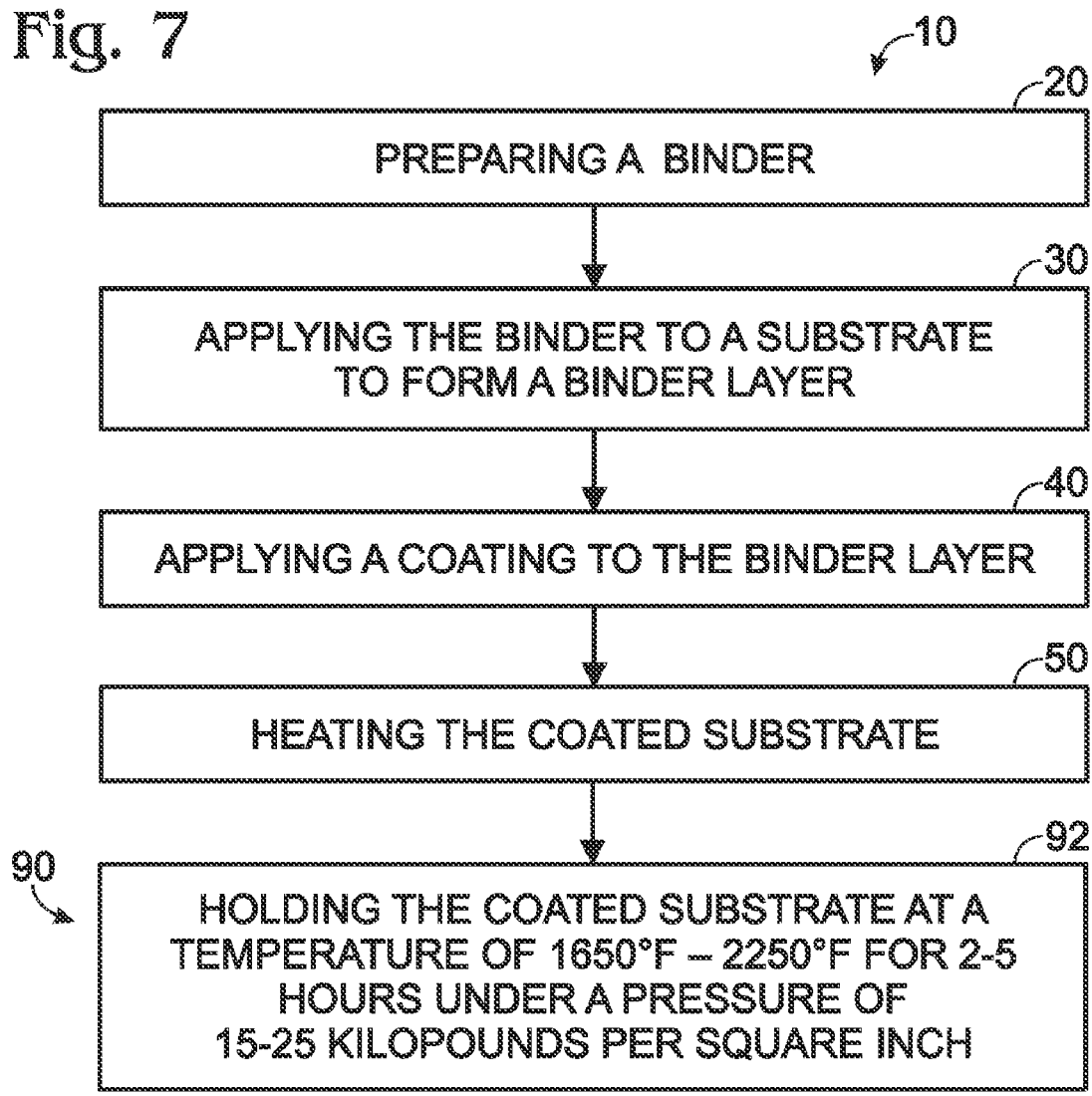

METHODS OF FORMING POROUS COATINGS ON SUBSTRATES

BACKGROUND

The surfaces of medical implants and other substrates are sometimes modified to impart desired properties to the medical implant or to enhance its existing properties. For example, with orthopedic implants, where bone attaches directly to the implant, it is often desirable to enhance the implant's ability to adhere and to integrate with bone. Increased adhesion and integration tends to reduce healing time and to improve long term fixation. In other examples, the surfaces of substrates are modified to improve the wear resistance of the substrate. Increased wear resistance is desirable when the substrate articulates against opposing components, such as the head of a femoral stem articulating against the surface of a femoral component of a knee replacement.

Medical implant substrates are often made of metals including titanium or cobalt because these metals have advantageous chemical, physical, and mechanical properties. For example, titanium and cobalt are considered biologically inert and resist corrosion. However, implants formed from these metals typically do not have surfaces that promote satisfactory bone adhesion and fixation.

To enhance the bone adhesion and fixation, porous coatings have been applied to these alloys. Porous coatings enhance adhesion and fixation with bone by providing pores into which bone will naturally grow. The bone growth extending through the pores of the implant results in a strong, intermeshed union of bone and implant.

Examples of porous coating methods are disclosed in the following U.S. patent and patent application references, which are hereby incorporated by reference for all purposes: U.S. Pat. Nos. 4,644,942, 4,854,496, 5,034,186, 5,104,410, 5,159,007, 5,211,775, 5,308,576, 5,443,510, 5,848,350, 6,261,322, 6,534,197, 6,725,901; 6,945,448, 20040133283, 20050048193, 20050196312, 20060004466, 20060052880, 20060285991, 20070065329; and 20070068340, 20070154620, 2007196230.

SUMMARY

The present disclosure is directed to methods of forming porous coatings on substrates. Methods of forming porous coatings include preparing a binder, applying the binder to a substrate to form a binder layer, applying a coating material to the binder layer to form a coating material layer, and sintering the coated substrate. In some examples, preparing a binder includes mixing together metal particles including titanium hydride or cobalt disilicide, a polymer including polybutene or poly-isobutylene, a brazing agent, and methyl cellulose. In some examples, the coating material includes titanium or cobalt. Applying the binder may include spray coating the binder onto the substrate.

BRIEF DESCRIPTION OF THE DRAWINGS

FIG. 1 is a flow chart of a method for forming a porous coating on a substrate.

FIG. 2 is a flow chart showing a more detailed example of the method of FIG. 1.

FIG. 3 is a flow chart showing the method of FIG. 1 including steps for forming a coating material including irregularly shaped particles.

FIG. 4 is a flow chart showing an example of forming a coating material feedstock.

FIG. 5 is a flow chart showing the method of FIG. 1 including steps for break-up-structure thermal processing.

FIG. 6 is a flow chart showing the method of FIG. 1 including steps for preparing a substrate to be coated.

FIG. 7 is a flow chart showing the method of FIG. 1 including steps for hot isostatic pressing thermal processing.

DETAILED DESCRIPTION

Figure 8:
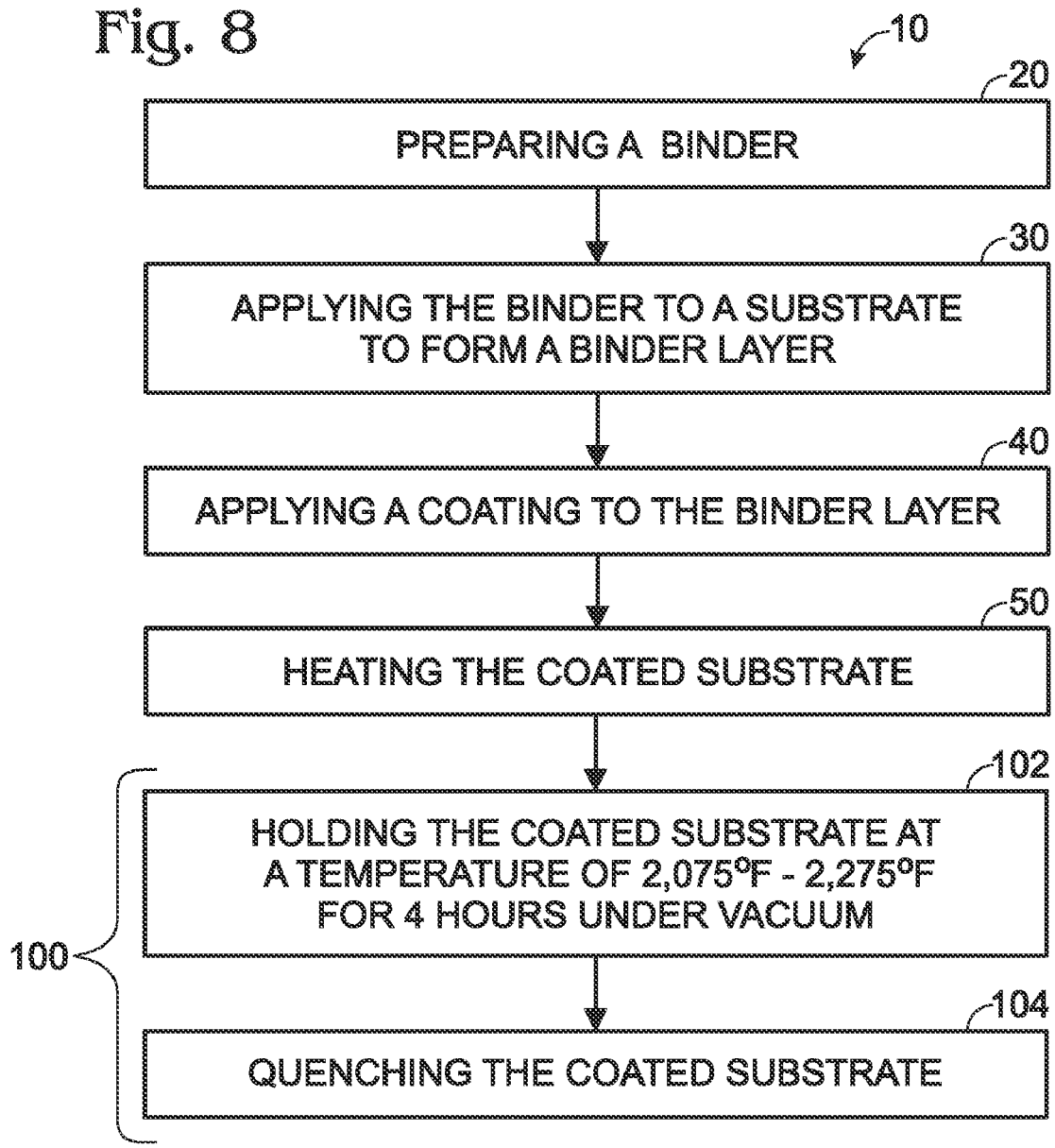
FIG. 8 is a flow chart showing the method of FIG. 1 including steps for solution heat treatment thermal processing.

The disclosed methods for forming porous coatings will become better understood through review of the following detailed description in conjunction with the drawings and the claims. The detailed description, drawings, and claims provide merely examples of the various inventions described herein. Those skilled in the art will understand that the disclosed examples may be varied, modified, and altered without departing from the scope of the inventions as defined in the claims, and all equivalents to which they are entitled. Many variations are contemplated for different applications and design considerations; however, for the sake of brevity, each and every contemplated variation is not individually described in the following detailed description.

As shown in FIG. 1, a method 10 for forming porous coatings on a substrate includes preparing a binder at step 20, applying the binder to a substrate to form a binder layer at step 30, applying a coating material to the binder layer at step 40, and heating the coated substrate at step 50. Throughout the description, examples of methods to form porous coatings on medical implants will be described. However, it is to be understood that the disclosed methods are equally applicable to forming porous coatings on a wide variety of substrates in addition to medical implants.

In the example shown in FIG. 2, preparing a binder 20 includes mixing together organic components, such as a liquid plastic, a brazing agent, and a thickener, at step 22. Preparing a binder 20 further includes adding binder metal particles to the organic components to form a binder at step 24. Mixing together the organic components 22 may be conducted at room temperature or at an elevated temperature.

In some examples, mixing together organic components 22 includes mixing the components together until the thickener dissolves. Adding binder metal particles to the organic components 24 may include mixing the binder until the binder metal particles are uniformly distributed. The binder may be continuously stirred to keep the metal particles uniformly distributed.

Each binder component has been found to contribute different properties to the binder. The binder may be formulated to have a suitable viscosity for being sprayed onto a substrate with a commercially available spray coating device. Additionally or alternatively, the binder may be formulated to bind coating material metal particles together for at least a period of time.

The binder metal particles have been found to increase the contact area between adjacent coating material particles and between coating material particles and the substrate. In some examples, generally spherical binder metal particles that are less than 50 μm are used. Contact area between the coating material particles is increased because these relatively small binder metal particles fit between the relatively large coating material metal particles and bridge gaps between them. Likewise, the contact area between the coating material particles and the substrate is increased because the relatively small binder metal particles bridge gaps between the coating material particles and the substrate.

Further, the binder metal particles have been observed to facilitate forming metallurgical bonds when the coated substrate is sintered. As small particles have a larger surface to volume ratio than large particles, they therefore require less energy to form metallurgical bonds when sintered. Thus, the relatively small binder metal particles help to form metallurgical bonds between the relatively large coating material metal particles at lower temperatures than would occur between the coating material particles without the binder metal particles.

It has been found that using titanium hydride particles in the binder is well suited when the coating material includes titanium hydride (and/or titanium hydride/dehydride) particles. At temperatures above 200° C., titanium hydride decomposes and hydrogen atoms evolve from it to form hydrogen gas. When the hydrogen gas is removed, pure titanium remains, which enables the binder particles, the coating material particles, and the substrate to fuse together well.

Similarly, using cobalt disilicide particles in the binder is well suited when the coating material includes cobalt-chrome-molybdenum particles. Cobalt disilicide ($CoSi_2$) is a relatively stable metal, and its composition is compatible with cobalt-chrome-molybdenum coating material particles. Often times, a substrate including cobalt is also used when the binder metal particles and the coating material metal particles include cobalt, which further provides chemical compatibility.

The liquid plastic in the binder provides liquidity, lubrication, and viscosity to the binder. In some examples, the polymer used in the binder includes polybutene, which is a viscous liquid plastic at room temperature. Other suitable polymers include polyurethanes, such as commercially available poly-isobutylene (PIB).

The brazing agent provides high temperature adhesion to help hold the coating material metal particles together up to approximately 1,000° F. In some examples, a brazing agent with a vaporization temperature of approximately 1,000° F. is selected. Sintering at a temperature above the brazing agent's vaporization temperature allows the brazing agent to be removed from the coated substrate by evaporation when sintering the coated substrate. For example, a peak sinter temperature of approximately 2,500° F. may be employed at step 50 in certain applications. Suitable brazing agents include nickel-based brazing agents.

The thickener has been observed to increase the viscosity of the binder, which improves the workability of the binder and facilitates applying the binder to the substrate. In some examples, the thickener includes methyl cellulose; however, other suitable thickeners may be used in different examples. Methyl cellulose has been found to impart suitable properties to the binder related to lubrication, thickening, and low temperature adhesion. Methyl cellulose also dissolves in certain polymers, such as poly-isobutylene.

The composition of the binder may vary depending on whether the metal powder includes titanium or cobalt. One binder composition includes 0.25-0.46 wt % titanium hydride, 0.32-0.54 wt % polybutene, 98.5-99.1 wt % of a nickel-based brazing agent, and 0.31-0.54 wt % methyl cellulose. In terms of exemplary actual quantities, these percentages may be achieved in a binder including 20-30 g titanium hydride, 30-40 ml polybutene, 800-1000 ml of a nickel-based brazing agent, and 25-35 g methyl cellulose. Further, fine titanium hydride particles of less than 50 μm are preferably used.

Another binder composition example includes 0.05-0.16 wt % cobalt disilicide, 0.10-0.26 wt % polybutene, 99.2-99.6 wt % of a nickel-based brazing agent, and 0.26-0.54 wt % methyl cellulose. In terms of exemplary actual quantities, these percentages may be achieved in a binder including 5-10 g cobalt disilicide, 10-20 ml polybutene, 800-1200 ml of a nickel-based brazing agent, and 25-35 g methyl cellulose. Further, fine cobalt-disilicide particles of less than 50 μm are preferably used.

As shown in FIG. 1, once the binder is prepared 20, the binder is applied to the substrate to form a binder layer 30. In the example shown in FIG. 2, applying the binder to the substrate 30 includes spray coating a portion of the binder onto the substrate to form an inner binder layer at step 32. In the FIG. 2 example, applying the binder to the substrate 30 also includes spray coating a portion of the binder onto a coating material layer, which was formed at step 40, to form at outer binder layer at step 34. Spray coating an outer binder layer onto the coating material layer serves to sandwich the coating material with layers of binder to help maintain the coating material in a desired position.

Spray coating the binder onto the substrate 32 or onto the coating material layer 34 may be accomplished with an air brush, such as an air brush set to 35 to 45 psi, or with other similar tools. Other techniques for applying the binder to the substrate 30 include brushing, pressing, and molding the binder onto the substrate. Any suitable molding method may be used, such as gravity, compression, or injection molding.

After forming the binder layer on the substrate 30, the coating material is applied to the binder layer 40. In the example shown in FIG. 2, applying a coating material to the binder layer 40 includes spreading coating particles over the inner binder layer at step 42. In some examples, spreading coating material particles over the inner binder layer at step 42 includes sprinkling metal particles onto the inner binder layer and then spreading the particles evenly over the binder layer. As discussed above, an outer binder layer may be applied to the coating material layer at step 34.

In some examples, multiple layers of coating material are applied to the substrate. In these examples, alternating layers of binder and coating material are applied to build up successive layers of coating material onto the substrate. Each layer of binder and coating material can be applied by the same means described above with regard to steps 30 and 40. Typically, the final layer applied will be an outer or covering layer of binder.

The coating material may include titanium or cobalt metal particles. For example, the coating material may include metal particles containing titanium, titanium alloy, cobalt, or cobalt alloy. In some examples, the coating material includes CP titanium hydride/dehydride particles or cobalt-chrome-molybdenum particles. The coating material may include regular metal particles, such as spherically shaped metal particles, or irregular metal particles, such as commercially available irregularly shaped particles. In the example shown in FIG. 3, the coating material includes irregularly shaped particles formed according to a method 60 for forming a coating material including irregularly shaped particles.

With reference to FIG. 3, method 60 for forming a coating material including irregularly shaped particles is described. The example of method 60 shown in FIG. 3 includes forming a coating material feedstock at step 62, injection molding the coating material feedstock into disks at step 64, granulating the disks into irregularly shaped particles at step 66, sorting the irregularly shaped particles by size at step 67, and heating selected irregularly shaped particles of a given size to form a coating material including irregularly shaped particles at step 68. As further shown in FIG. 3 at step 40, the coating material including irregularly shaped particles formed by method 60 is applied to the binder layer.

With reference to FIG. 4, a particular example of forming a coating material feedstock 62 is described. In the FIG. 4 example, forming a coating material feedstock 62 includes adding an aromatic hydrocarbon and a lubricant to a vessel at step 621 and heating and mixing the vessel contents at step 622.

With further reference to the example shown in FIG. 4, forming a coating material feedstock 62 includes adding a thermoplastic to the vessel at step 623 and adding spherical metal particles of titanium or cobalt to the vessel at step 624. The vessel contents are mixed until the viscosity of the coating material feedstock remains constant at step 625. At step 626, the coating material feedstock is cooled to cause the coating material feedstock to solidify. At step 627, the coating material feedstock is granulated to break it into convenient sized pieces.

In some examples, the coating material feedstock mixing vessel is sealed to prevent evaporation of components. Additionally or alternatively, the coating material feedstock mixing vessel may include a variable speed mixing blade with a sealed shaft. The vessel can be heated to specified temperatures, such as temperatures above the melting point of the aromatic hydrocarbon, using any conventional heating system. Any known temperature control method may be employed.

In some examples, naphthalene is used as an aromatic hydrocarbon. However, the aromatic hydrocarbon can be any number of aromatic compounds. Aromatic hydrocarbons having relatively low melting and/or sublimation temperatures may be particularly suitable. For example, naphthalene melts at 176° F. and sublimates at room temperature. Aromatic hydrocarbons serve to help retain the shape of the coating material feedstock after it is injected into a mold that defines a desired shape. Preferably, the aromatic hydrocarbon is removable when the coating material feedstock is heated to a relatively low temperature.

Stearic acid has been found to be an acceptable lubricant for use at step 621. The lubricant facilitates removing the coating material feedstock from the mold after being injected into a mold. The lubricant also improves the flow characteristics of the coating material feedstock. Organic, fatty acids, such as stearic acid, are suitable lubricants. Additionally or alternatively, the lubricant may include solid waxes, such as microcrystalline waxes.

As thermoplastics generally remain in a solid state at room temperature, they can lend strength to the coating material feedstock. It has been observed that thermoplastics help maintain the shape of the coating material feedstock when it has been molded into a desired shape. A suitable thermoplastic composition is 5-15 vol. % of the coating material feedstock. In some examples, a thermoplastic composition of 8-12 vol. % of the coating material feedstock is targeted.

Any of a variety of thermoplastics may be used in the coating material feedstock at step 623 to strengthen the molded article. In some examples, polystyrene is used. Additionally or alternatively to polystyrene, suitable thermoplastics include ethylene vinyl acetate, polyethylene, and butadiene.

In some examples, 10-50 μm spherical particles of titanium hydride are used at step 624. In other examples, 10-50 μm spherical particles of cobalt-chrome-molybdenum are used at step 624. The composition of the coating material feedstock may very depending on whether titanium or cobalt metal particles are used.

In one example, the composition of the coating material feedstock is 1-10 vol % lubricant, 5-15 vol % thermoplastic, 28-32 vol % aromatic hydrocarbon, with the remaining volume being 10-50 μm spherical particles of titanium hydride. In some examples, approximately 45-70 vol. % titanium hydride is used. In certain examples, 8-12 vol. % thermoplastic is targeted.

In another example, the composition of the coating material feedstock is 1-10 vol. % lubricant, 8-12 vol. % thermoplastic, 28-32 vol. % aromatic hydrocarbon, with the remaining volume being 10-50 μm spherical particles of cobalt-chrome-molybdenum. In some examples, approximately 45-70 vol. % cobalt-chrome-molybdenum is used. 8-12 vol. % thermoplastic may be targeted.

At step 623, the thermoplastic may dissolve in approximately 10 minutes, such as when the thermoplastic is polystyrene. Adding spherical metal particles 624 and mixing until a uniform viscosity is obtained at step 625 may be performed while the coating material feedstock is held at approximately 200° F.

Granulating the coating material feedstock at step 627 may include stirring the coating material feedstock as it solidifies during cooling. Alternatively, granulating the coating material feedstock may including discharging the coating material feedstock onto a metal sheet, allowing it to cool and solidify, and then grinding it into small pieces. Coating material feedstock pieces of a size suitable for injection molding, such as approximately 5 to 10 mm$^3$, may be obtained by granulating the coating material feedstock at step 627. After granulating the coating material feedstock, it may be stored in a sealed container.

Shifting attention back to FIG. 3, injection molding the coating material feedstock into disks or pellets at step 54 in one example produces disks or pellets with a thickness of 0.25" and a diameter of 1". A variety of metal injection molding techniques may be used, such as those described in Applicant's copending U.S. patent application Ser. No. 11/941,018 (issued as U.S. Pat. No. 7,883,662), which is hereby incorporated by reference for all purposes. Any type of injection molding machine compatible with the composition and properties of the coating material feedstock may be used. Injection molding machines usually include a barrel, a die cavity (mold), a hydraulic pressure system, and control system.

Injection molding the coating material feedstock into disks or pellets at step 64 may include selecting barrel and mold temperatures, selecting how long to hold the coating material feedstock in the mold, and selecting the pressure used to inject the coating material feedstock into the mold. Maintaining the barrel of the injection molding machine at a selected temperature heats the coating material feedstock within the barrel to a related temperature by conduction. Similarly, maintaining the mold at a relatively cold temperature cools the coating material feedstock in the mold by conduction and causes it to solidify.

In some examples, a barrel temperature slightly higher than the melting point of the aromatic hydrocarbon is selected. For example, when the aromatic hydrocarbon is naphthalene, a barrel temperature of not more than 200° F. is selected. Higher barrel temperatures can undesirably cause the composition of coating material feedstock to change and can cause gas bubbles to form within the coating material feedstock, which can cause structural defects within the molded article.

Pressures of 100 to 1,000 psi are suitable for injecting the coating material feedstock into a mold. In some examples, the coating material feedstock is pressurized to approximately 400-500 psi. It has been observed that pressurizing the coating material feedstock to more than 1000 psi can sometimes damage the mold and result in improperly molded articles.

Once the coating material feedstock is injected into the mold, it is allowed to solidify in the mold by being cooled to a temperature sufficiently low to cause it to freeze. In some examples, the mold is maintained at a temperature of not more than 120° F., such as a temperature of not more than 90° F. or a temperature between 50 and 90° F. In one example, a mold temperature of 70° F. is targeted.

Solidification times can range between 1 second and 1 minute, depending on the quantity of coating material feedstock in the mold. Solidification times longer than a minute can occur when higher mold temperatures are used. After the coating material feedstock has solidified, it is removed from the mold. The coating material feedstock can be molded into a variety of shapes, including disks or pellets, which can be easily granulated into small particles.

Granulating the disks or pellets at step 66 forms irregularly shaped particles. Manual or automatic grinders may be used. As the disks or pellets are in a low strength "green" state, they typically can be ground relatively easily. In some examples, irregularly shaped particles ranging in size between 100 and 2000 microns are produced by granulating the disks or pellets at step 66.

In some examples, sorting the irregularly shaped particles by size at step 67 includes sieving the particles through different screens to sort the particles into different size distributions. Sieving the particles may include passing the irregularly shaped particles through a stack of screens supported on a vibration generator. In some examples, the stack of screens includes 30, 45, 60, 80, and 100 mesh screens, which select for a particle size range of approximately 100-400 microns. Sieving may be completed in as little as 10-15 minutes in some examples.

Sieving the particles may occur prior to heating the particles to remove the aromatic hydrocarbon, the lubricant, and the thermoplastic. Sieving the particles before heating at step 68 can facilitate keeping the particles intact when sorting them by size.

Different particle size distributions of the irregular shaped particles are selected depending on the desired porosity characteristics for the coating. Relevant porosity characteristics can include the average pore size or the percentage of pores in the coating as a whole. In some examples, certain amounts of different particle size distributions are combined into a batch for use in the coating.

In some examples, heating the irregularly shaped particles at step 68 includes removing 70-85% of the non-metal particle components of the coating material feedstock. For example, 75-80% of the aromatic hydrocarbon and 50-60% of the lubricant may be removed while substantially all of the thermoplastic remains. In other examples, substantially all non-metal particle components are removed by heating at step 68. In either instance, any remaining non-metal particle components, such as the thermoplastic, may be removed when heating the coated substrate at step 50.

In some examples, heating the particles at step 68 includes monitoring the particles to measure how much non-metal particle components have been removed. Heating the particles at step 68 may include two different heating cycles: a first cycle to remove 75-80% of the non-metal particle components of the coating material feedstock and a second cycle to substantially remove the remainder of the non-metal particle components.

In one example, heating at step 68 includes holding the irregularly shaped particles at 80-100° F. under a pressure of 500-1000 microns Hg for 6-30 hours. In other examples, heating the irregularly shaped particles at step 68 includes holding the particles at 100-120° F. under ambient pressure for 6-30 hours.

If a second heating cycle is to be performed, heating the particles at step 68 includes heating the particles to approximately 300° F. to substantially remove any remaining non-metal particle components, such as the lubricant. In each example of heating at step 68, the irregularly shaped particles may be placed on a zirconia or yttria support, which are support materials that inhibit oxygen pick-up by the particles during heating. After heating the irregularly shaped particles at step 68, the particles are used as coating material particles to be applied to the binder layer at step 40.

Shifting attention back to FIGS. 1 and 2, heating the coated substrate at step 50 is described in further detail. Heating the coated substrate at step 50 may include sintering the coated substrate by heating it to 2350-2600° F. for at least 3 hours at step 52. Heating the coated substrate at step 50 may be conducted under vacuum or at ambient pressure.

Different sintering temperatures may be selected for different coating material and substrate materials. Generally, sintering is conducted at a peak temperature below the melting point of the substrate material. Further, the coated substrate may be heated at step 50 for different amounts of time depending on factors including the coating material and the substrate material, the heating temperature, and the pressure used while heating.

For example, when the coating material includes titanium metal particles and the substrate is titanium, the coated substrate may be held at 2475-2575° F. for 9-11 hours under vacuum. In some examples, the coated substrate is held at approximately 2,530° F. for 10 hours under 220 microns of partial pressure. Alternatively, when the coating material includes cobalt-chrome metal particles and the substrate is a cobalt-chrome-molybdenum alloy, the coated substrate may be held at 2350-2450° F. for 3-5 hours under vacuum. In some examples, the coated substrate is held at 2,390° F. for 4 hours under 250 microns of partial pressure.

In some examples, heating the coated substrate at step 50 is conducted at positive or atmospheric pressure instead of under vacuum. When heating is conducted at a non-vacuum pressure, heating may be conducted in the presence of an inert gas. As is well known in the art, heating a reactive metal in an inert gas environment may help to avoid undesired oxidation reactions between the metal and oxygen that can occur in an air environment.

In the example shown in FIG. 5, method 10 includes break-up-structure thermal processing at step 70. Break-up-structure thermal processing 70 is used to reduce the substrate's grain size. It has been observed that the substrate's grain size can increase when the coated substrate is sintered.

Materials with small grain size tend to have improved fatigue strength. Improved fatigue strength occurs because small grain size increases the proportion of grain boundaries in a volume of material and grain boundaries tend to resist fatigue. To further change the mechanical and physical properties of the coated substrate after break-up-structure thermal processing 70, the coated substrate may be annealed by maintaining it at approximately 1550° F. for approximately 4 hours.

As shown in FIG. 5, one example of break-up-structure thermal processing 70 includes holding the temperature of the coated substrate at 1850-1950° F. for 0.5-1.5 hours at step 72. In some examples, the coated substrate is held at approximately 1880° F. for 45-60 min under 200 microns of partial pressure. After step 72, the coated substrate in the example of FIG. 5 is held at 1500-1600° F. for 7-9 hours at step 74. In some examples, the coated substrate is held at approximately 1550° F. for 8 hours. Break-up-structure thermal processing 70 includes quenching the coated substrate at step 76.

Quenching the coated substrate at step 76 may include cooling the coated substrate from 1500-1600° F. to 150-350° F. at a rate of 75-325° F./min. In some examples, quenching the coated substrate at step 76 includes cooling the coated substrate to 200-250° F. at a rate of 100-300° F./min. To rapidly cool the coated substrate, argon or helium gas may be introduced via a fan to serve as a heat convecting fluid to exchange heat with a heat exchanger.

In the example shown in FIG. 6, method 10 includes preparing the substrate to receive a coating at step 80. Preparing the substrate at step 80 has been observed to improve the coating process, for example, by increasing the surface area of the substrate, which provides more contact area to which the coating material may bond. Preparing the substrate to receive a coating at step 80 includes roughening the substrate at step 82 and cleaning the substrate at step 84.

In some examples, roughening the substrate at step 82 includes blasting the substrate with abrasives. For example, roughening the substrate at step 82 may include sandblasting the substrate at 40-80 psi in a blast chamber. A wide variety of ceramic particles may be used as the abrasive. Aluminum oxide is one suitable ceramic particle to use as the abrasive.

In one example, cleaning the substrate at step 84 includes an ultrasonic soap and water bath held at a temperature of 180-200° F. In other examples, cleaning the substrate at step 84 simply involves a hot water bath. Additionally or alternatively, cleaning the substrate at step 84 may include soaking the substrate in alcohol and drying the substrate.

With reference to FIG. 7, an example of method 10 including hot isostatic pressing at step 90 is described. It has been observed that elevated sintering temperatures can cause voids to form in the substrate at high energy locations due to incipient melting. High energy locations in the substrate include grain boundaries and positions adjacent second phase precipitates.

Hot isostatic pressing 90 serves to strengthen the coated substrate by reducing voids formed in the substrate. Hot isostatic pressing 90 reduces voids and consolidates the coating with the substrate by exerting high pressure on the coated substrate at high temperatures. Preferably, the pressure is applied to the coated substrate uniformly from all sides.

In the example shown in FIG. 7, hot isostatic pressing 90 includes holding the coated substrate at a temperature of 1650-2,250° F. for 2-5 hours under a pressure of 15-25 kilopounds per square inch at step 92. A variety of additional or alternative temperature ranges may be used. Further, pressures higher and lower than 15-25 kilopounds per square inch may be employed as appropriate for different coated substrates.

An example of method 10 including a solution heat treatment at step 100 is shown in FIG. 8. Solution heat treatment 100 serves to dissolve precipitates of second phase particles, such as intermetallic particles and carbides. Further, solution heat treatment 100 allows alloying elements present in the coated substrate to uniformly mix.

Elevated temperatures are used in solution heat treatment 100 to allow the alloying elements to uniformly distribute throughout the base metal particles in a manner akin to a solution. Rapid cooling then inhibits precipitation of second phases and fixes the alloying elements in their uniformly dispersed positions. Solution heat treatment 100 may also soften or anneal the coated substrate to improve its ductility.

In the example shown in FIG. 8, solution heat treatment 100 includes heating the coated substrate to a temperature of 2,075-2,275° F. for 4 hours under vacuum at step 102. Solution heat treatment 100 also includes quenching the coated substrate at step 104. In one example, quenching the coated substrate includes cooling the coated substrate from 2,075-2,275° F. to 100-200° F. at a rate greater than or equal to 75° F./min. However, quenching may involve cooling the coated substrate to an alternative target temperature range, such as to room temperature.

Property data for substrates with porous coatings formed from method 10 described above is provided in Table 1. Six samples were produced in each of six different production runs. The samples were tested for weight gain, tensile strength, pore area percent, and pore size. The weight gain measured was the difference in weight between the uncoated substrate and the coated substrate. The average test result for all six samples in each run are provided below in Table 1 for each property.

TABLE 1

Property Data

| | Property Tested | | | | | | | |
|---|---|---|---|---|---|---|---|---|
| | Weight Gain (g) | | Tensile Strength (psi) | | Pore area (%) | | Pore Size (μm) | |
| Production Run | Average | Standard Deviation | Average | Standard Deviation | Average | Standard Deviation | Average | Standard Deviation |
| Run 1 | 0.62 | 0.04 | 6587 | 297 | 67.0 | 5.4 | 336 | 243 |
| Run 2 | 0.63 | 0.05 | 6847 | 141 | 67.0 | 5.8 | 400 | 307 |
| Run 3 | 0.60 | 0.00 | 7328 | 146 | 64.2 | 6.2 | 251 | 201 |
| Run 4 | 0.57 | 0.05 | 7349 | 82 | 66.4 | 4.9 | 258 | 203 |
| Run 5 | 0.60 | 0.09 | 6519 | 434 | 60.6 | 6.2 | 254 | 165 |
| Run 6 | 0.62 | 0.04 | 6579 | 437 | 66.5 | 7.3 | 266 | 232 |

It is believed that the disclosure set forth above encompasses multiple distinct inventions with independent utility. While each of these inventions has been disclosed in a particular form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Where the disclosure or subsequently filed claims recite "a" or "a first" element or the equivalent thereof, it is within the scope of the present inventions that such disclosure or claims may be understood to include incorporation of one or more such elements, neither requiring nor excluding two or more such elements.

Applicant reserves the right to submit claims directed to certain combinations and subcombinations that are directed to one or more of the disclosed inventions and that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to a different invention or directed to the same invention, whether different, broader, narrower or equal in scope to the original claims, are also regarded as included within the subject matter of the inventions of the present disclosure.

What is claimed is:

1. A method of forming a porous coating on a substrate comprising:
    preparing a binder by mixing together:
        metal particles including titanium hydride or cobalt disilicide,
        a polymer including polybutene or poly-isobutylene,
        a brazing agent, and
        methyl cellulose;
    applying the binder to the substrate to form a binder layer;
    applying a coating material that includes titanium or cobalt to the binder layer to form a coating material layer, the binder layer and the coating material layer being applied to the substrate defining a coated substrate; and
    sintering the coated substrate.

2. The method of claim 1, wherein preparing a binder includes mixing together:
    0.25-0.46 wt % titanium hydride;
    0.32-0.54 wt % polybutene;
    98.5-99.1 wt % brazing agent; and
    0.31-0.54 wt % methyl cellulose.

3. The method of claim 1, wherein preparing a binder includes mixing together:
    0.052-0.16 wt % cobalt disilicide;
    0.10-0.26 wt % polybutene;
    99.2-99.6 wt % brazing agent; and
    0.26-0.54 wt % methyl cellulose.

4. The method of claim 1, wherein applying the binder to the substrate includes spray coating at least a portion of the binder onto the substrate to form the binder layer.

5. The method of claim 4, wherein applying the coating material to the binder layer includes spreading at least a portion of the coating material onto the binder layer to form the coating material layer.

6. The method of claim 5, further comprising spray coating a further portion of the binder onto the coating material layer to form a binder cover layer.

7. The method of claim 6, further comprising spreading a further portion of the coating material onto the binder cover layer to form a second coating material layer.

8. The method of claim 1, wherein sintering the coated substrate includes holding the coated substrate at a temperature of 2350-2600° F. for at least 3 hours.

9. The method of claim 8, wherein sintering the coated substrate includes holding the coated substrate at a temperature of 2475-2575° F. for at least 3 hours under vacuum.

10. The method of claim 9, wherein sintering the coated substrate is performed for 9-11 hours.

11. The method of claim 8, wherein sintering the coated substrate includes holding the coated substrate at a temperature of 2350-2450° F. under vacuum for at least 3 hours.

12. The method of claim 11, wherein sintering the coated substrate is performed for 3-5 hours.

13. The method of claim 1, wherein the brazing agent includes nickel.

14. The method of claim 1, wherein the coating material includes irregularly shaped titanium hydride particles or irregularly shaped cobalt-chromium-molybdenum particles.

15. The method of claim 14, further comprising
    forming a coating material feedstock comprising regularly shaped titanium hydride particles or regularly shaped cobalt-chromium-molybdenum particles, an aromatic hydrocarbon, a thermoplastic, and a lubricant;
    injection molding the coating material feedstock into disks;
    granulating the disks into irregularly shaped particles; and
    holding the irregularly shaped particles under vacuum at a temperature of 80-100° F.

16. The method of claim 15, wherein the titanium hydride particles or the cobalt-chromium-molybdenum particles have a particle size less than 50 μm.

17. The method of claim 15, wherein the aromatic hydrocarbon consists of naphthalene and the thermoplastic consists of polystyrene.

18. The method of claim 15, wherein the coating material feedstock includes:
    45-70 vol. % titanium hydride or cobalt-chromium-molybdenum particles;
    28-32 vol. % aromatic hydrocarbon;
    5-15 vol. % thermoplastic; and
    1-10 vol. % lubricant.

19. The method of claim 15, further comprising sorting the irregularly shaped particles by size and selecting a group of irregularly shaped particles having a given size prior to holding the irregularly shaped particles under vacuum at a temperature of 80-100° F.

20. The method of claim 15, further comprising heating the irregularly shaped coating material particles to 300° F. until a preselected amount of the aromatic hydrocarbon, the thermoplastic, or the lubricant has been removed.

21. The method of claim 1, further comprising:
    holding the temperature of the coated substrate at 1850-1950° F. for 0.5-1.5 hours;
    holding the temperature of the coated substrate at 1500-1600° F. for 7-9 hours; and
    cooling the coated substrate from 1500-1600° F. to 150-350° F. at a rate of 75-325° F./min.

22. The method of claim 1, further comprising blasting the substrate with abrasives prior to applying the binder to the substrate.

23. The method of claim 1, further comprising cleaning the substrate in a fluid bath subject to ultrasonic waves.

24. The method of claim 1, further comprising holding the coated substrate at a temperature of 1,650-2,250° F. under a pressure of 15-25 kilopounds per square inch for 2-5 hours.

25. The method of claim 1, further comprising:
    holding the coated substrate at a temperature of 2,075-2,275° F. under vacuum for 4 hours; and
    cooling the coated substrate from 2,075-2,275° F. to 100-200° F. at a rate greater than or equal to 75° F./min.

26. A method of forming a porous coating on a substrate comprising:
    forming a binder including metal particles, which include titanium hydride or cobalt disilicide, a polymer including polybutene or poly-isobutylene, a brazing agent, and a thickener including methyl cellulose;
    spray coating a first portion of the binder onto the substrate to form an inner binder layer;

spreading a coating material including metal particles including titanium or cobalt onto the inner binder layer to form a coating material layer;

spray coating a second portion of the binder onto the substrate to form a coated substrate;

and holding the coated substrate at 2350-2600° F. for at least 3 hours.

* * * * *